(12) United States Patent
Deng et al.

(10) Patent No.: US 8,846,723 B2
(45) Date of Patent: Sep. 30, 2014

(54) ESTERS OF O-SUBSTITUTED HYDROXY CARBOXYLIC ACIDS AND PREPARATIONS THEREOF

(75) Inventors: Liu Deng, Kingsport, TN (US); Neil Warren Boaz, Kingsport, TN (US); Sabine Delaire, Rueil Malmaison (FR)

(73) Assignees: Eastman Chemical Company, Kingsport, TN (US); Chanel Parfums Beaute, Neuilly-sur-Seine (FR)

( * ) Notice: Subject to any disclaimer, the term of this patent is extended or adjusted under 35 U.S.C. 154(b) by 148 days.

(21) Appl. No.: 12/975,572

(22) Filed: Dec. 22, 2010

(65) Prior Publication Data

US 2012/0029198 A1    Feb. 2, 2012

Related U.S. Application Data

(60) Provisional application No. 61/368,850, filed on Jul. 29, 2010.

(51) Int. Cl.
| | |
|---|---|
| *A61K 31/4406* | (2006.01) |
| *A61K 31/221* | (2006.01) |
| *A61K 31/235* | (2006.01) |
| *C07C 69/76* | (2006.01) |
| *C07C 69/734* | (2006.01) |
| *C07C 403/20* | (2006.01) |
| *C07C 403/12* | (2006.01) |
| *C07C 67/11* | (2006.01) |
| *A61Q 19/08* | (2006.01) |
| *A61K 8/67* | (2006.01) |
| *A61Q 19/00* | (2006.01) |
| *C12P 7/62* | (2006.01) |
| *C07C 67/03* | (2006.01) |
| *C07D 309/40* | (2006.01) |
| *A61Q 19/02* | (2006.01) |

(52) U.S. Cl.
CPC .............. *C07D 309/40* (2013.01); *A61Q 19/02* (2013.01); *C07C 69/734* (2013.01); *C07C 403/20* (2013.01); *C07C 403/12* (2013.01); *C07C 67/11* (2013.01); *A61Q 19/08* (2013.01); *A61K 8/671* (2013.01); *C07C 2101/16* (2013.01); *A61Q 19/00* (2013.01); *C12P 7/62* (2013.01); *C07C 67/03* (2013.01); *A61Q 19/002* (2013.01)
USPC ............... 514/356; 514/551; 514/528; 560/73

(58) Field of Classification Search
CPC ...... C07C 69/88; C07C 69/75; C07C 69/732; A61K 8/671; A61K 31/60; A61K 31/455
See application file for complete search history.

(56) References Cited

U.S. PATENT DOCUMENTS

| | | | | |
|---|---|---|---|---|
| 2,302,618 | A | * | 11/1942 | Loder ............................ 560/187 |
| 2,518,456 | A | * | 8/1950 | Fein et al. ...................... 560/185 |
| 4,107,290 | A | | 8/1978 | Jacquet et al. |
| 4,812,457 | A | * | 3/1989 | Narumiya et al. ......... 514/226.2 |
| 5,605,933 | A | | 2/1997 | Duffy et al. |
| 5,972,323 | A | | 10/1999 | Lang et al. |
| 6,572,882 | B1 | | 6/2003 | Vercauteren et al. |
| 7,030,265 | B2 | | 4/2006 | Sin et al. |
| 7,098,246 | B2 | | 8/2006 | Geelings et al. |
| 7,102,019 | B2 | | 9/2006 | Streicher et al. |
| 7,670,606 | B2 | | 3/2010 | Volkmann |
| 7,671,009 | B2 | | 3/2010 | Ludin et al. |
| 8,029,810 | B2 | | 10/2011 | Skold |
| 2003/0225160 | A1 | | 12/2003 | Geerlings et al. |
| 2005/0015058 | A1 | | 1/2005 | Millerd |
| 2005/0095232 | A1 | | 5/2005 | Volkmann |
| 2009/0035236 | A1 | | 2/2009 | Maes et al. |
| 2009/0035237 | A1 | | 2/2009 | Maes et al. |

(Continued)

FOREIGN PATENT DOCUMENTS

| | | |
|---|---|---|
| CN | 1455780 A | 11/2003 |
| CN | 1620446 A | 5/2005 |

(Continued)

OTHER PUBLICATIONS

Zaragoza Dorwald, Side Reactions in Organic Synthesis, 2004, Wiley-VCH Verlag GmbH & Co. KGaA, Weinheim, Preface. p. IX.*

(Continued)

*Primary Examiner* — Paul A Zucker
(74) *Attorney, Agent, or Firm* — Phan Law Group PLLC

(57) ABSTRACT

Esters of O-substituted hydroxy carboxylic acids are provided having Formula 1, or 2, or both Formulas 1 and 2:

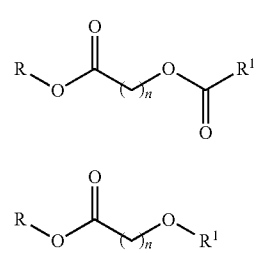

wherein R and $R^1$ are independently selected from the group consisting of substituted and unsubstituted, branched- and straight-chain, saturated, unsaturated, and polyunsaturated $C_1$-$C_{22}$ alkyl, substituted and unsubstituted $C_3$-$C_8$ cycloalkyl, substituted and unsubstituted $C_6$-$C_{20}$ carbocyclic aryl, and substituted and unsubstituted $C_4$-$C_{20}$ heterocyclic; wherein the heteroatoms are selected from sulfur, nitrogen, and oxygen; and wherein n is 1-6. Process of producing esters of O-substituted hydroxy carboxylic acids are also provided.

12 Claims, 1 Drawing Sheet

(56) References Cited

U.S. PATENT DOCUMENTS

| | | | |
|---|---|---|---|
| 2009/0035240 | A1 | 2/2009 | Maes et al. |
| 2009/0035242 | A1 | 2/2009 | Maes et al. |
| 2009/0035243 | A1 | 2/2009 | Czarnota et al. |
| 2009/0068132 | A1 | 3/2009 | Bratescu et al. |
| 2010/0035986 | A1 | 2/2010 | Maeda et al. |

FOREIGN PATENT DOCUMENTS

| | | | |
|---|---|---|---|
| CN | 101772482 | A | 7/2010 |
| DE | 2 311 346 | | 10/1973 |
| DE | 4415204 | | 11/1995 |
| EP | 0 342 055 | A2 | 11/1989 |
| EP | 1 498 104 | A1 | 1/2005 |
| EP | 2 072 494 | A1 | 6/2009 |
| ES | 2 233 208 | | 6/2005 |
| ES | 2 246 603 | | 2/2006 |
| FR | 2 436 602 | A1 | 4/1980 |
| FR | 2 919 800 | | 2/2009 |
| JP | 2002 193752 | A | 7/2002 |
| JP | 2005 041871 | A | 2/2005 |
| KR | 829890 | * | 5/2008 |
| WO | 95 16659 | A1 | 6/1995 |
| WO | 97 20812 | A1 | 6/1997 |
| WO | 02/055540 | | 7/2002 |
| WO | 2004 054992 | A1 | 7/2004 |
| WO | 2005/019156 | | 3/2005 |
| WO | 2005 108534 | A1 | 11/2005 |
| WO | WO 2007/030464 | A2 * | 3/2007 |
| WO | 2007 053794 | A2 | 5/2007 |
| WO | 2009/018389 | | 2/2009 |
| WO | 2009 156324 | A2 | 12/2009 |
| WO | 2011/041487 | | 4/2011 |

OTHER PUBLICATIONS

Murai et al, Kogyo Kagaku Zasshi, 1959, 62, pp. 1094-1098, English abstract.*
International Search Report from Int'l Appl. No. PCT/US2011/045303, pp. 1-6 (Sep. 23, 2011).
International Search Report from Int'l App. No. PCT/US2012/025335, pp. 1-4 (May 21, 2012).
Database Registry [Online], Chemical Abstracts Service, Columbus, Ohio, US; Jun. 8, 2008, XP002676266, Database accession No. 1026294-10-9, abstract.
Co-pending U.S. Appl. No. 12/975,562, filed Dec. 22, 2010; Neil Boaz.
Co-pending U.S. Appl. No. 61/379,929, filed Sep. 3, 2010; Neil Boaz.
Co-pending U.S. Appl. No. 13/031,375, filed Feb. 21, 2010.
Maugard, Thierry and Legoy, Marie Dominique; "Enzymatic Synthesis of Derivatives of Vitamin A in Organic Media"; Journal of Molecular Catalysis B: Enzymatic 8; 2000; pp. 275-280.
Maugard, Thierry et al; "Study of Vitamin Ester Synthesis by Lipase-Catalyzed Transesterification in Organic Media"; Biotechnol. Prog.; 2000; vol. 16; pp. 358-362.
Maugard, Thierry et al; "Synthesis of Water-Soluble Retinol Derivatives by Enzymatic Method"; Biotechnol. Prog.; 2002; vol. 18; pp. 424-428.
O'Connor, Charmian J. et al; "*Candida cylindracea* Lipase-Catalysed Synthesis of Retinyl and Oleyl Palmitates; Carbon ChainLength Dependence of Esterase Activity"; Aust. J. Chem.; 1992; vol. 45; pp. 641-649.
Stryer, Lubert; "Acetoacetate is a Major Fuel in Some Tissues"; Biochemistry, Fourth Edition; 1995; Chapter 24, p. 613.

English translation of KR 10-0829890 B1, pp. 1-23 (May 16, 2008).
Chankeshwara, Sunay V., et al., "Organocatalytic Methods for Chemoselective O-tert-Butoxycarbonylation of Phenols and Their Regeneration from the O-t-Box Derivatives," J. Org. Chem., vol. 73, No. 21 (2008), pp. 8615-8618.
Kittisak, Likhitwitayawuid, et al., "Structure Modification of Oxyresveratol for tyrosinase inhibitory activity," Researches Assisted by the Asahi Glass Foundation, Reports, XX, JP, (2008), p. 60. (Abstract).
Charvat, Trevor T., et al., "Design, synthesis, and biological evaluation of chicoric acid analogs as inhibitors of HIV-1 integrase," Bioorg. & Med. Chem., vol. 14, (2006), pp. 4552-4567.
Bratt, Mark O., et al., "Synthesis of Carbonates and Related Compounds from Carbon Dioxide via Methanesulfonyl Carbonates," J. Org. Chem., vol. 68, No. 14, (2003), pp. 5439-5444.
Dikusar, E. A., et al., "Methyl-and Ethyl Carbonates Derived from Vanillin and Vanillal in the Synthesis of Nitrogen-containing Compounds," Russian J. Gen. Chem., vol. 77, No. 5, (2007), pp. 905-910.
Jones, Ryan M., et al., "Rapid Syntheses of Benzopyrans from o-OBOC Salicylaldehydes and Salicyl alcohols: A Three-Component Reaction," J. Org. Chem., vol. 67, No. 20, (2002), pp. 6911-6915.
Carafa, Marianna, et al., "Superbase-promoted direct N-carbonylation of pyrrole with carbonic acid diesters," Tetrahedron Letters, Elsevier, Amsterdam, NL, vol. 49, No. 22, (2008), pp. 3691-3696.
Hirakawa, Takuya, et al., "A Magentically Separable Heterogeneous Deallylation Catalyst: [CpRu(n3-C3H5)(2-pyridinecarboxylato)]PF6 Complex Supported on a Ferromagnetic Microsize Particle Fe3O4@SiO2," European J. Org. Chem., vol. 2009, No. 6, (2009), pp. 789-792.
Hallman, Kristina, et al., "Enantioselective allylic alkylation using polymer-supported palladium catalysts," Tetrahedron: Asymmetry, vol. 10, No. 20, (1999), pp. 4037-4046.
Ouchi, Hidekazu, et al., "1-tert-Butoxy-2-tert-butoxycarbonyl-1,2-dihydroisoquinoline: A Novel and Chemoselective tert-Butoxycarbonylation Reagent," Org. Ltrs., vol. 4, No. 4, (2002), pp. 585-587.
Cuny, Gregory D., et al., "Solution-Phase Ring Opening Cross-Metathesis of Bicyclic Alkenes with Styrene Derivatives and Its Application to 'Resin Capture' Solid-Phase Synthesis," Tetrahedron, Elsevier Science Publishers, Amsterdam, NL, vol. 55, No. 27, (1999), pp. 8169-8178.
Buisman, G. J. H., et al., "Enzymatic esterifications of functionalized phenols for the synthesis of lipophilic antioxidants," Biotech. Ltrs., vol. 20, No. 2, (1998), pp. 131-136.
Gordon, Michael H., et al., "Antioxidant Activity of Hydroxytyrosol Acetate Compared with That of Other Olive Oil Polyphenols," J. Agr. Food Chem., vol. 49, (2001), pp. 2480-2485.
Grasso, Salvatore, et al., "Hydroxytyrosol lipophilic analgoues: Enzymatic synthesis, radical scavenging activity and DNA oxidative damage protection," Bioorg. Chem., vol. 35, (2007), pp. 137-152.
Mateos, Raquel, et al., "New Lipophilic Tyrosyl Esters. Comparative Antioxidant Evaluation with Hydroxytyrosyl Esters," J. Agr. Food Chem., vol. 56, (2008), pp. 10960-10966.
Trujillo, Mariana, et al., "Lipophilic Hydroxytyrosyl Esters. Antioxidant Activity in Lipid Matrices and Biological Systems," J. Agr. Food Chem., vol. 54, (2006), pp. 3779-3785.
International Search Report from Int'l Appl. No. PCT/US2011/049047, pp. 1-6 (Nov. 17, 2011).
Kim, Sungbum, et al., "Synthesis and in vitro biological activity of retinyl polyhydroxybenzoates, novel hydrid retinoid derivatives," Bioorg. & Med. Chem. Ltrs., vol. 19, (2009), pp. 508-512.
English translation of Search Report from State Intellectual Property Office of People's Republic of China issued in counterpart Application No. 2011 80 047 315.6. filed on Jul. 26, 2011, pp. 1-3.

* cited by examiner

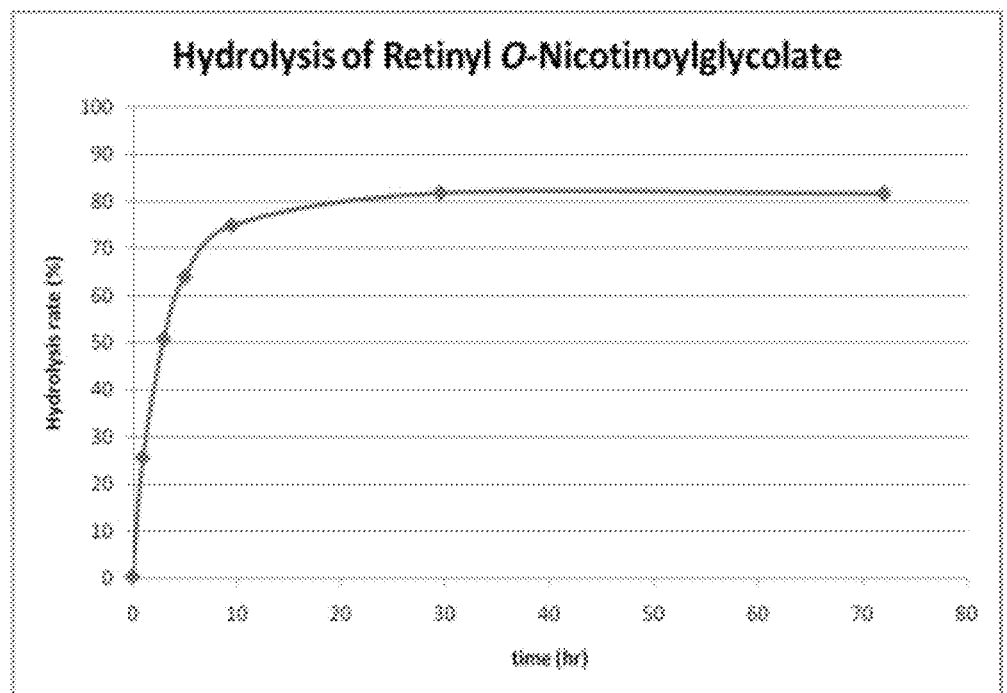

ESTERS OF O-SUBSTITUTED HYDROXY CARBOXYLIC ACIDS AND PREPARATIONS THEREOF

CROSS REFERENCES TO RELATED APPLICATIONS

This application is an original application claiming priority to provisional application U.S. Ser. No. 61/368,850 filed Jul. 29, 2010, herein incorporated by reference to the extent it does not contradict the statements herein.

FIELD OF THE INVENTION

The present invention pertains to the field of esters of O-substituted hydroxy carboxylic acids. The invention also pertains to processes for producing O-substituted hydroxy carboxylic acids.

SUMMARY OF FIGURES

FIG. 1 shows the extent of hydrolysis over time in Example 15.

BACKGROUND OF THE INVENTION

Retinol (Vitamin A) and its derivatives have a long history as active ingredients in cosmetic compositions to improve the overall appearance of the skin. Retinol itself is unstable and is toxic upon excessive use. Long-chain retinyl esters are sometimes preferred because they are more stable and less irritating to the skin. These esters are expected to be readily hydrolyzed in the skin to afford retinol for metabolism and thus efficacy. Depending on the fatty acids, the hydrolysis product may introduce additional benefits too. Besides fatty acids, other structures, with various biological properties, are also desired in retinyl conjugates in order to improve and/or broaden the biological benefits. Thus, a mild and general method is needed to link retinol or other skin care ingredients with interesting structures.

The most commonly used chemical preparation of esters involves the reaction of an alcohol and an acid chloride or anhydride (activated carboxylate) in the presence of a base. Nucleophilic substitution of a carboxylate on an alkyl halide or sulfonate is another effective method, provided that the halide or sulfonate is readily available. In the case of retinyl esters, both routes proved to be suboptimal since retinol and retinyl esters tend to be unstable under these types of reaction conditions.

There have been several reports of chemical and enzymatic syntheses of retinyl esters. The preparation of a retinol-ascorbic acid conjugate has been described in the literature where the two substructures are connected by a glycolate linker using a two-step chemical route. Enzymatic esterification or trans-esterification preparation of retinyl esters are usually catalyzed by native or modified enzymes. These reactions generally only afford incomplete conversion to the desired retinyl ester product unless the by-product is removed from the reaction by the use of a large amount of molecular sieves, using reduced pressure, and/or by purging the reaction mixture with an inert gas. The substrate specificity of many enzymes generally limits this type of transformation to straight-chain carboxylic acids, especially fatty acids. Since the synthesis and hydrolysis of esters are catalyzed by the same family of enzymes, i.e. lipases, esters that cannot be enzymatically prepared are less likely to be readily hydrolyzed by enzymes in the skin to release the active agent retinol. Although in some cases it is possible to esterify retinol by chemical methods with challenging species, such as branched carboxylic acids or other sterically-hindered species, these esters might only offer marginal efficacy since they still need to be hydrolyzed in the skin to release retinol to be effective. Thus, a process for conjugating retinol or other skin care ingredients with a broad variety of species which would release retinol in vivo would be of interest.

A specially-designed linker, which is used to connect skin care ingredients with a variety of species, can be envisioned to solve this challenge. It would be highly desirable that this connection occur under mild conditions and in high yield. This would allow the preparation of conjugates of skin care ingredients and other species that are difficult to directly connect. More importantly, this linker should also facilitate the enzymatic ester hydrolysis and thus the ready release of the free skin care ingredient in the skin.

SUMMARY OF THE INVENTION

In one embodiment of this invention, an ester of O-substituted hydroxy carboxylic acids is provided having Formula 1 or Formula 2,

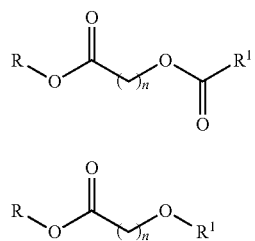

wherein R and $R^1$ are independently selected from the group consisting of substituted and unsubstituted, branched- and straight-chain, saturated, unsaturated, and polyunsaturated $C_1$-$C_{22}$ alkyl, substituted and unsubstituted $C_3$-$C_8$ cycloalkyl, substituted and unsubstituted $C_6$-$C_{20}$ carbocyclic aryl, and substituted and unsubstituted $C_4$-$C_{20}$ heterocyclic; wherein the heteroatoms are selected from sulfur, nitrogen, and oxygen; and wherein n is 1-6.

In another embodiment of the invention, a process is provided to produce at least one ester of an O-substituted hydroxy carboxylic acid having Formula 1, or 2:

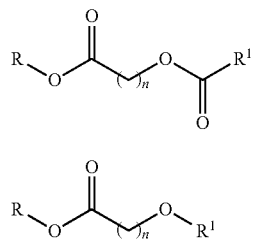

wherein R and $R^1$ are independently selected from the group consisting of substituted and unsubstituted, branched- and straight-chain, saturated, unsaturated, and polyunsaturated $C_1$-$C_{22}$ alkyl, substituted and unsubstituted $C_3$-$C_8$ cycloalkyl, substituted and unsubstituted $C_6$-$C_{20}$ carbocyclic aryl, and substituted and unsubstituted $C_4$-$C_{20}$ heterocyclic; wherein the heteroatoms are selected from sulfur, nitrogen, and oxygen; and wherein n is 1-6, the process comprising:

a) contacting an alcohol having Formula 3

R—OH     3 with a terminal halogen-substituted straight-chain carboxylic acid having Formula 4

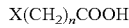
$X(CH_2)_nCOOH$     4 or a short-chain ester having Formula 5

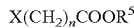
$X(CH_2)_nCOOR^5$     5 in the presence of an enzyme to produce an intermediate having the Formula 6,

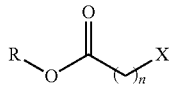

6 wherein R is independently selected from the group consisting of substituted and unsubstituted, branched- and straight-chain, saturated, unsaturated, and polyunsaturated $C_2$-$C_{22}$ alkyl, substituted and unsubstituted $C_3$-$C_8$ cycloalkyl, substituted and unsubstituted $C_6$-$C_{20}$ carbocyclic aryl, and substituted and unsubstituted $C_4$-$C_{20}$ heterocyclic; wherein the heteroatoms are selected from sulfur, nitrogen, and oxygen; wherein $R^5$ is a straight or branched $C_1$-$C_4$-alkyl or alkenyl, X is a halogen atom, and n is 1-6;

b) reacting the intermediate with a carboxylic acid or alcohol optionally in the presence of a base and optionally in the presence of a catalyst to produce at least one ester of Formula 1 or 2.

DETAILED DESCRIPTION

In one embodiment of this invention, novel compounds have been discovered represented by the general formulas 1 and 2:

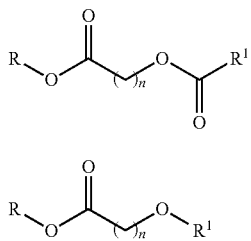

wherein R and $R^1$ are independently selected from substituted and unsubstituted, branched- and straight-chain, saturated, unsaturated, and polyunsaturated $C_1$-$C_{22}$ alkyl, substituted and unsubstituted $C_3$-$C_8$ cycloalkyl, substituted and unsubstituted $C_6$-$C_{20}$ carbocyclic aryl, and substituted and unsubstituted $C_4$-$C_{20}$ heterocyclic wherein the heteroatoms are selected from sulfur, nitrogen, and oxygen and n is 1-6.

In another embodiment, R and $R^1$ are independently selected from the group consisting of substituted and unsubstituted, branched- and straight-chain saturated $C_1$-$C_{22}$ alkyl, substituted and unsubstituted, branched- and straight-chain $C_2$-$C_{22}$ alkenyl, substituted and unsubstituted, branched- and straight-chain $C_4$-$C_{22}$ dienyl, substituted and unsubstituted, branched- and straight-chain $C_6$-$C_{22}$ trienyl, substituted and unsubstituted, branched- and straight-chain $C_8$-$C_{22}$ tetraenyl, substituted and unsubstituted, branched- and straight-chain $C_{10}$-$C_{22}$ pentaenyl, substituted and unsubstituted $C_3$-$C_8$ cycloalkyl, substituted and unsubstituted $C_4$-$C_{20}$ heterocyclic, or mixtures thereof, and n is 1-6.

The alkyl, alkenyl, dienyl, trienyl, tetraenyl, pentaenyl, and cycloalkyl groups which may be represented by R and $R^1$ may be straight- or branched-chain aliphatic hydrocarbon radicals containing up to about 22 carbon atoms and may be substituted, for example, with one to five groups selected from $C_1$-$C_6$-alkoxy, carboxyl, amino, $C_1$-$C_{15}$ aminocarbonyl, $C_1$-$C_{15}$ amido, cyano, $C_2$-$C_6$-alkoxycarbonyl, $C_2$-$C_6$-alkanoyloxy, hydroxy, aryl, heteroaryl, thiol, thioether, $C_2$-$C_{10}$ dialkylamino, $C_3$-$C_{15}$ trialkylammonium and halogen. The terms "$C_1$-$C_6$-alkoxy", "$C_2$-$C_6$-alkoxycarbonyl", and "$C_2$-$C_6$-alkanoyloxy" are used to denote radicals corresponding to the structures —$OR^2$, —$CO_2R^2$, and —$OCOR^2$, respectively, wherein $R^2$ is $C_1$-$C_6$-alkyl or substituted $C_1$-$C_6$-alkyl. The terms "$C_1$-$C_{15}$ aminocarbonyl" and "$C_1$-$C_{15}$ amido" are used to denote radicals corresponding to the structures —NHCOR$^3$, —CONHR$^3$, respectively, wherein $R^3$ is $C_1$-$C_{15}$-alkyl or substituted $C_1$-$C_{15}$-alkyl. The term "$C_3$-$C_8$-cycloalkyl" is used to denote a saturated, carbocyclic hydrocarbon radical having three to eight carbon atoms. The branching and/or substitution of R and $R^1$ may connect to form a ring.

The aryl groups which R and $R^1$ may represent (or any aryl substituents) may include phenyl, naphthyl, or anthracenyl and phenyl, naphthyl, or anthracenyl substituted with one to five substituents selected from $C_1$-$C_6$-alkyl, substituted $C_1$-$C_6$-alkyl, $C_6$-$C_{10}$ aryl, substituted $C_6$-$C_{10}$ aryl, $C_1$-$C_6$-alkoxy, halogen, carboxy, cyano, $C_1$-$C_6$-alkanoyloxy, $C_1$-$C_6$-alkylthio, $C_1$-$C_6$-alkylsulfonyl, trifluoromethyl, hydroxy, $C_2$-$C_6$-alkoxycarbonyl, $C_2$-$C_6$-alkanoylamino and —$OR^4$, —S—$R^4$, —$SO_2$—$R^4$, —$NHSO_2R^4$ and —$NHCO_2R^4$, wherein $R^4$ is phenyl, naphthyl, or phenyl or naphthyl substituted with one to three groups selected from $C_1$-$C_6$-alkyl, $C_6$-$C_{10}$ aryl, $C_1$-$C_6$-alkoxy and halogen.

The heterocyclic groups which R and $R^1$ may represent (or any heteroaryl substituents) include 5- or 6-membered ring containing one to three heteroatoms, excluding ascorbic acid. The heteroatoms are independently selected from the group consisting of oxygen, sulfur and nitrogen. Examples of such heterocyclic groups are pyranyl, oxopyranyl, dihydropyranyl, oxodihydropyranyl, tetrahydropyranyl, thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, pyridyl, pyrimidyl, benzoxazolyl, benzothiazolyl, benzimidazolyl, indolyl and the like. The heterocyclic radicals may be substituted, for example, with up to three groups such as $C_1$-$C_6$-alkyl, $C_1$-$C_6$-alkoxy, substituted $C_1$-$C_6$-alkyl, halogen, $C_1$-$C_6$-alkylthio, aryl, arylthio, aryloxy, $C_2$-$C_6$-alkoxycarbonyl and $C_2$-$C_6$-alkanoylamino. The heterocyclic radicals also may be substituted with a fused ring system, e.g., a benzo or naphtho residue, which may be unsubstituted or substituted, for example, with up to three of the groups set forth in the preceding sentence. The term "halogen" is used to include fluorine, chlorine, bromine, and iodine.

In another embodiment of the invention, R can be retinyl and $R^1$ can be any of the radicals previously described in this disclosure.

Examples of the compounds of the invention include those represented by Formula 1; wherein n is 1, R—O is retinyl or oleyl and $R^1CO$ are carnitinoyl, shikimoyl, 4-methoxycinnamoyl, feruloyl, salicyloyl, nicotinoyl, retinoyl or 2-cyano-3,3-diphenylacryloyl, and formula 2 wherein n is 1, R—O is retinyl and $R^1$ is 2-hydroxymethyl-4H-pyran-4-on-5-yl.

The novel chemoenzymatic process of our invention involves 2 steps. The first step comprises the enzymatic reaction of an alcohol 3:

with a terminal halogen-substituted straight-chain carboxylic acid $X(CH_2)_nCOOH$ or short-chain ester $X(CH_2)_nCOOR^5$ in the presence of an enzyme with or without methods for the removal of the water or alcohol by-product to form the desired intermediate 4, wherein R is defined as above, $R^5$ is a straight or branched $C_1$-$C_4$-alkyl or alkenyl, X is a halogen atom and n is 1-6.

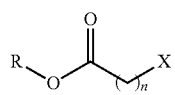

The first step of the process is carried out without solvent, or in an inert solvent chosen from cyclic or acyclic ether solvents, such as, diethyl ether, diisopropyl ether, tert-butyl methyl ether, or tetrahydrofuran; aromatic hydrocarbons, such as, benzene, toluene, or xylene; aliphatic or alicyclic saturated or unsaturated hydrocarbons, such as, hexane, heptane, cyclohexane, or limonene; halogenated hydrocarbons, such as, dichloromethane, dichloroethane, dibromoethane, tetrachloroethylene, or chlorobenzene; polar aprotic solvents, such as, acetonitrile, dimethyl formamide, or dimethyl sulfoxide; or mixtures thereof. In one embodiment, no solvent is utilized in the first step. In another embodiment, at least one inert solvent is utilized selected from the group consisting of toluene, limonene, heptanes, and acetonitrile. The first step of the process may be carried out at a temperature between about −100° C. to about 100° C. In another embodiment, the first step of the process can be carried out at a temperature between about −100° C. to the boiling point of the inert solvent. Other temperature ranges are from about 0° C. to about 60° C. and from about 20° C. to about 50° C. The amount of halogen-substituted acid or short-chain ester may be between about 0.85 and about 20 equivalents based on the weight of the compound of Formula 3. Other amounts of halogen-substituted acid or short-chain ester range from about 1 and about 10 equivalents and from about 1 to about 1.5 equivalents.

The enzyme used in the first step of the process is chosen from a protease, a lipase, or an esterase. In one embodiment, the enzyme is a lipase. These lipases may be in the form of whole cells, isolated native enzymes, or immobilized on supports. Examples of these lipases include, but are not limited to, Lipase PS (from *Pseudomonas* sp), Lipase PS-C (from *Psuedomonas* sp immobilized on ceramic), Lipase PS-D (from *Pseudomonas* sp immobilized on diatomaceous earth), Lipoprime 50T, Lipozyme TL IM, or Novozym 435 (*Candida antarctica* lipase B immobilized on acrylic resin). The amount of enzyme can range from about 0.01 to about 200 wt % based on the alcohol of Formula 3. The amount of enzyme can also range from about 0.1 to about 50 wt % based on the alcohol of Formula 3.

In the first step of the process, removal of the water or alcohol byproducts can be done chemically via a water or alcohol absorbent (e.g., molecular sieves) or by physical removal of the water or alcohol. This by-product removal can be conducted by evaporation, either by purging the reaction mixture with an inert gas such as nitrogen, argon, or helium, or by performing the reaction at reduced pressures, or both, as these conditions can afford >98% conversion of retinol to Intermediate 4. The pressure for the reaction can be between 1 torr and ambient pressure or between 50 torr and ambient pressure. Any inert solvent that is included in the first step of this process may or may not be removed along with the water or alcohol. Examples of Formula 3 R—OH include, but are not limited to, retinol and oleyl alcohol.

The second step to generate the ester of o-substituted hydroxyl carboxylic acid Formula 1 comprises the reaction of Intermediate 4 with the desired carboxylic acid or alcohol optionally in the presence of a base. The second step of the process is carried out without solvent or in an inert solvent chosen from water, cyclic or acyclic ether solvents, such as, but not limited to, diethyl ether, diisopropyl ether, tert-butyl methyl ether, or tetrahydrofuran; aromatic hydrocarbons, such as, benzene, toluene, or xylene; aliphatic or alicyclic saturated or unsaturated hydrocarbons, such as, hexane, heptane, cyclohexane, or limonene; halogenated hydrocarbons, such as, dichloromethane, dichloroethane, dibromoethane, tetrachloroethylene, or chlorobenzene; ester solvents, such as methyl acetate, ethyl acetate, methyl propionate, or isopropyl acetate; polar aprotic solvents, such as, acetonitrile, dimethyl formamide, or dimethyl sulfoxide, or mixtures thereof. In another embodiment of the invention, no solvent is utilized. In another embodiment, at least one inert solvent is utilized selected from the group consisting of tetrahydrofuran, dimethyl formamide, dimethyl sulfoxide, acetone, acetonitrile, ethyl acetate, toluene, water, and mixtures thereof.

The second step of the process may be carried out at a temperature between about −100° C. and about 100° C. In another embodiment, the second step of the process can be carried out at a temperature between about −100° C. and the boiling point of the inert solvent. Other temperature ranges are from about 0° C. to about 60° C. and from about 20° C. to about 50° C. The amount of the acid or alcohol may be between about 0.85 and about 20 equivalents based on Intermediate 4. Other ranges are from about 1 to about 10 equivalents or from about 1 to about 1.5 equivalents.

If included, the base is chosen from tertiary amines, metal hydroxides, metal alkoxides, metal carbonates, or metal bicarbonates. In one embodiment, at least one base is selected from the group consisting of triethylamine, N,N-diisopropylethylamine, sodium hydroxide, potassium hydroxide, sodium carbonate, potassium carbonate, and potassium bicarbonate. The amount of base can be from about 0.4 molar equivalents to about 20 molar equivalents based on the ester of Formula 4. In another embodiment, the amount is between about 0.5 and about 10 equivalents or between about 0.5 and about 1.5 equivalents.

The second step of the process may also include the presence of a catalyst chosen from quaternary ammonium salts, quaternary phosphonium salts, or crown ethers. Examples of such catalysts include, but are not limited to, tetrabutylammonium bromide, tetraheptylammonium bromide, tetraheptylammonium chloride, methyl tribuylammonium chloride, methyl tricaprylammonium chloride, tetrabutylphosphonium chloride, and 12-crown-6. The amount of catalyst may be between about 0.005 and about 1.0 molar equivalents based on the ester of Formula 4. Another range is from about 0.01 to about 0.5 equivalents.

The intermediate of Formula 3 and the esters of O-substituted hydroxy carboxylic acids of Formulas 1 and 2 of the process may be isolated using methods known to those of skill in the art, e.g., extraction, filtration, or crystallization.

The esters of O-substituted hydroxy carboxylic acids can be utilized in compositions, such as cosmetic compositions, skin care compositions and the like. The compositions can be useful, for example, for reducing skin roughness, fine lines, and wrinkles, improving photo-damaged skin, regenerating skin, reducing skin hyper-pigmentation, and reducing irritation and/or inflammatory reaction in skin.

Typical cosmetic and/or skin care compositions of the invention contain at least 0.001% by weight of the O-substituted hydroxy carboxylic acids according to the present invention. For example, the compositions can contain from about 0.001% to about 20.0% by weight or from about 0.01 to about 10.0% by weight of the O-substituted hydroxy carboxylic acids according to the present invention. Lower concentrations may be employed for less pronounced conditions, and higher concentrations may be employed with more acute conditions. Suggested ranges also depend upon any adjunct ingredients employed in the compositions.

The cosmetic and skin care compositions of the invention may also contain other skin conditioning ingredients in addition to O-substituted hydroxy carboxylic acids. Such compositions may also contain other skin ingredients such as retinol, retinyl esters, tetronic acid, tetronic acid derivatives, hydroquinone, kojic acid, gallic acid, arbutin, α-hydroxyl acids, and fatty acid esters of ascorbic acid. Such other ingredients are known to those of skill in the art.

Typically, topical application to skin sites is accomplished in association with a carrier. Where employed, the carrier is inert in the sense of not bringing about a deactivation or oxidation of active or adjunct ingredient(s), and in the sense of not bringing about any adverse effect on the skin areas to which it is applied. For example, the compounds according to the present invention are applied in admixture with a dermatologically acceptable carrier or vehicle (e.g., as a lotion, cream, ointment, soap, stick, or the like) so as to facilitate topical application and, in some cases, provide additional beneficial effects as might be brought about, e.g., by moisturizing of the affected skin areas. Many preparations are known in the art, and include lotions containing oils and/or alcohols and emollients such as olive oil, hydrocarbon oils and waxes, silicone oils, other vegetable, animal or marine fats or oils, glyceride derivatives, fatty acids or fatty acid esters or alcohols or alcohol ethers, lecithin, lanolin and derivatives, polyhydric alcohols or esters, wax esters, sterols, phospholipids and the like, and generally also emulsifiers (nonionic, cationic or anionic). These same general ingredients can be formulated into a cream rather than a lotion, or into gels, or into solid sticks by utilization of different proportions of the ingredients and/or by inclusion of thickening agents such as gums or other forms of hydrophilic colloids.

The novel processes provide by the present invention are further illustrated by the following examples.

Example 1

Preparation of Retinyl Bromoacetate

To an amber round bottle, retinol in toluene (59.7 wt % retinol; 30.65 g; 18.30 g retinol; 63.9 mmol) was added followed by methyl bromoacetate (10.75 g; 70.2 mmol; 1.1 equiv.) and Novozym 435 (0.46 g). The mixture was stirred at room temperature and purged with a stream of nitrogen through the mixture for 26 hours to afford 96.7% conversion of retinol to intermediate 4 according to HPLC analysis. The mixture was filtered, and the solid was washed with heptanes. The filtrate was concentrated to give the desired product as a viscous yellow oil (25.32 g, 97%). Intermediate 4 was used in the subsequent reactions without further purification.

HPLC (High Performance Liquid Chromatography) (4.6× 150 mm Zorbax SB-C8 column [Agilent], 3.5μ thickness, 95:5 methanol:water (containing 0.1% trifluoroacetic acid) for 10 min, detection at 325 nm): $t_R$ 3.7 min (retinol); $t_R$ 4.9 min (retinyl bromoacetate).

Example 2

Preparation of Retinyl O-Carnitinoylglycolate Bromide

Carnitine inner salt (0.65 g, 4 mmol) was suspended in dimethylformamide (3 mL). Retinyl bromoacetate (1.628 g; 4 mmol) in dimethyl formamide (2 mL) was added dropwise. The mixture was stirred at room temperature for 5 hours to afford >99% conversion of retinyl bromoacetate to the ester according to HPLC analysis. The mixture was filtered and concentrated in vacuo to give 2.2 g of a yellow, very hygroscopic solid. $^1$H NMR (Hydrogen-1-Nuclear Magnetic Resonance) (CDCl$_3$) δ (ppm): 6.67 (dd, 1H, J=15.0, 11.4 Hz), 6.27 (d, 1H, J=15.0 Hz), 6.3-6.0 (m, 3H), 5.57 (t, 1H, J=7.2 Hz), 4.9-4.7 (m, 2H), 4.68 (d, 2H, J=2.4 Hz), 3.9-3.7 (m, 2H), 3.45 (br s, 9H), 3.0-2.8 (m, 4H), 2.02 (t, 2H, J=6.6 Hz), 1.96 (s, 3H), 1.89 (s, 3H), 1.71 (s, 3H), 1.65-1.55 (m, 2H), 1.5-1.4 (m, 2H), 1.02 (s, 6H).

HPLC (4.6×150 mm Zorbax SB-C8 column [Agilent], 3.5μ thickness, 95:5 methanol:water (containing 0.1% trifluoroacetic acid) for 10 min, detection at 325 nm): $t_R$ 2.0 min (retinyl O-carnitinoylglycolate bromide); $t_R$ 5.1 min (retinyl bromoacetate).

Example 3

Preparation of Retinyl O-Feruloylglycolate

Ferulic acid (2.913 g; 15 mmol) was mixed with potassium carbonate (1.036 g; 7.5 mmol) in dimethyl formamide (30 mL). The mixture was stirred for 45 min, then retinyl bromoacetate (6.112 g; 15 mmol) was added dropwise. The mixture was stirred overnight to afford >99% conversion of retinyl bromoacetate to the ester according to HPLC analysis. The mixture was then diluted with toluene (300 mL) and washed with water and brine repeatedly. The organic phase was dried and concentrated in vacuo to give the desired product as a yellow solid (7.95 g; 93%). $^1$H NMR (CDCl$_3$) δ (ppm): 7.70 (d, 1H, J=15.9 Hz), 7.09 (dd, 1H, J=8.1, 1.8 Hz), 7.04 (d, 1H, J=1.8 Hz), 6.92 (d, 1H, J=8.1 Hz), 6.67 (dd, 1H, J=15.0, 11.4 Hz), 6.38 (d, 1H, J=16.2 Hz), 6.27 (d, 1H, J=15.3 Hz), 6.3-6.0 (m, 3H), 5.61 (t, 1H, J=7.2 Hz), 4.85 (d, 2H, J=7.2 Hz), 4.75 (s, 2H), 3.92 (s, 3H), 2.02 (t, 2H, J=6.3 Hz), 1.96 (s, 3H), 1.90 (s, 3H), 1.71 (s, 3H), 1.65-1.55 (m, 2H), 1.5-1.4 (m, 2H), 1.02 (s, 6H).

HPLC (4.6×150 mm Zorbax SB-C8 column [Agilent], 3.5μ thickness, 95:5 methanol:water (containing 0.1% trifluoroacetic acid) for 10 min, detection at 325 nm): $t_R$ 4.3 min (retinyl O-feruloylglycolate); $t_R$ 4.8 min (retinyl bromoacetate).

Example 4

Preparation of Retinyl O-Shikimoylglycolate

Shikimic acid (2.606 g; 15 mmol) was mixed with potassium carbonate (1.046 g; 7.5 mmol) in dimethyl sulfoxide (20 mL). The mixture was stirred for 45 min and then placed in a cold bath. At 12° C., retinyl bromoacetate (6.023 g; 14.5 mmol) in dimethyl sulfoxide (10 mL) was added dropwise. The mixture was stirred for 2 hours to afford 98% conversion of retinyl bromoacetate to the ester according to HPLC analysis. The mixture was then diluted with ethyl acetate (150 mL) and washed with water and brine repeatedly. The organic phase was dried and concentrated in vacuo to give the desired product as a yellow solid (6.573 g; 91%). $^1$H NMR (CDCl$_3$) δ (ppm): 6.96 (br s, 1H), 6.65 (dd, 1H, J=15.0, 11.4 Hz), 6.26 (d, 1H, J=15.0 Hz), 6.2-6.0 (m, 3H), 5.58 (t, 1H, J=7.2 Hz), 4.81 (d, 2H, J=7.5 Hz), 4.69 (s, 2H), 4.5-4.4 (m, 1H), 4.05-3.95 (m, 1H), 3.7-3.6 (m, 1H), 2.95-2.95 (m, 1H), 2.3-2.2 (m, 1H), 2.01 (t, 2H, J=6.0 Hz), 1.95 (s, 3H), 1.88 (s, 3H), 1.71 (s, 3H), 1.65-1.55 (m, 2H), 1.5-1.4 (m, 2H), 1.02 (s, 6H).

HPLC (4.6×150 mm Zorbax SB-C8 column [Agilent], 3.5μ thickness, 95:5 methanol:water (containing 0.1% trifluoroacetic acid) for 10 min, detection at 325 nm): $t_R$ 3.0 min (retinyl O-shikimoylglycolate); $t_R$ 4.7 min (retinyl bromoacetate).

Example 5

Preparation of Retinyl O-(4-Methoxycinnamoyl)glycolate

4-Methoxycinnamic acid (4.296 g; 24 mmol) was mixed with potassium carbonate (1.665 g; 12 mmol) in dimethyl formamide (15 mL). The mixture was stirred for 5 min and placed in a cold bath. At −8° C., retinyl bromoacetate (10.805 g; 26.5 mmol) in dimethyl formamide (15 mL) was added dropwise. The mixture was stirred overnight at room temperature. The mixture was then diluted with ethyl acetate (200 mL) and washed with water, 10% K$_2$CO$_3$ and brine repeatedly. The organic phase was dried and concentrated in vacuo to give the desired product as a yellow viscous oil (10.321 g; 85%). $^1$H NMR (CDCl$_3$) δ (ppm): 7.74 (d, 1H, J=15.6 Hz), 7.50 (d, 2H, J=9.3 Hz), 6.91 (d, 2H, J=9.0 Hz), 6.66 (dd, 1H, J=15.0, 11.4 Hz), 6.40 (d, 1H, J=15.6 Hz), 6.28 (d, 1H, J=15.0 Hz), 6.2-6.0 (m, 3H), 5.62 (t, 1H, J=7.8 Hz), 4.85 (d, 2H, J=6.9 Hz), 4.74 (s, 2H), 3.84 (s, 3H), 2.02 (t, 2H, J=6.0 Hz), 1.96 (s, 3H), 1.90 (s, 3H), 1.71 (s, 3H), 1.65-1.55 (m, 2H), 1.5-1.4 (m, 2H), 1.02 (s, 6H).

HPLC (4.6×150 mm Zorbax SB-C8 column [Agilent], 3.5μ thickness, 95:5 methanol:water (containing 0.1% trifluoroacetic acid) for 10 min, detection at 325 nm): $t_R$ 3.0 min (retinyl O-(4-methoxycinnamoyl)glycolate); $t_R$ 4.7 min (retinyl bromoacetate).

Example 6

Preparation of Retinyl O-(2-Hydroxymethyl-4H-pyran-4-on-5-yl)glycolate

Kojic acid (142 mg; 1.0 mmol) was mixed with potassium carbonate (69 mg; 0.50 mmol) in dimethyl formamide (5 mL). Retinyl bromoacetate (421 mg; 1.03 mmol) was added dropwise. The mixture was stirred for 5 hours. The mixture was then diluted with ethyl acetate and washed with water twice. The organic phase was dried and concentrated in vacuo to give the desired product as a yellow viscous oil (548 mg). $^1$H NMR (CDCl$_3$) δ (ppm): 8.02 (s, 1H), 6.67 (dd, 1H, J=15.0, 11.4 Hz), 6.55 (s, 1H), 6.28 (d, 1H, J=15.0 Hz), 6.2-6.0 (m, 3H), 5.61 (t, 1H, J=7.8 Hz), 4.85 (d, 2H, J=5.4 Hz), 4.73 (s, 2H), 4.49 (s, 2H), 2.02 (t, 2H, J=6.0 Hz), 1.98 (s, 3H), 1.91 (s, 3H), 1.73 (s, 3H), 1.65-1.55 (m, 2H), 1.5-1.4 (m, 2H), 1.04 (s, 6H).

HPLC (4.6×150 mm Zorbax SB-C8 column [Agilent], 3.5μ thickness, 95:5 methanol:water (containing 0.1% trifluoroacetic acid) for 10 min, detection at 325 nm): $t_R$ 3.4 min (retinyl O-(2-hydroxymethyl-4H-pyran-4-on-5-yl)glycolate); $t_R$ 5.4 min (retinyl bromoacetate).

Example 7

Preparation of Retinyl O-Salicyloylglycolate

Salicylic acid (4.576 g; 33.1 mmol) was mixed with potassium carbonate (2.093 g; 15.1 mmol) in dimethyl formamide (18 mL). The mixture was stirred for 5 min and then placed in an ice bath. At 0° C., retinyl bromoacetate (12.221 g; 30.0 mmol) in dimethyl formamide (12 mL) was added dropwise. The mixture was stirred overnight at room temperature. More salicylic acid (414 mg, 3.0 mmol) and more potassium carbonate (414 mg, 3.0 mmol) were added. The mixture was stirred for another 7 hours at room temperature. The mixture was then diluted with diethyl ether (150 mL) then washed with water (15 mL×2), 10% potassium bicarbonate (15 mL) and brine (15 mL). The organic phase was dried and concentrated in vacuo to give the desired product as a yellow solid (13.351 g; 96%). $^1$H NMR (CDCl$_3$) δ (ppm): 7.93 (dd, 1H, J=8.1, 1.8 Hz), 7.55-7.45 (m, 1H), 7.02-6.98 (m, 1H), 6.94-6.87 (m, 1H), 6.67 (dd, 1H, J=15.0, 11.4 Hz), 6.27 (d, 1H, J=15.0 Hz), 6.2-6.0 (m, 3H), 5.61 (t, 1H, J=7.5 Hz), 4.87 (d, 2H, J=7.2 Hz), 4.87 (s, 2H), 2.02 (t, 2H, J=6.0 Hz), 1.96 (s, 3H), 1.90 (s, 3H), 1.71 (s, 3H), 1.65-1.55 (m, 2H), 1.5-1.4 (m, 2H), 1.02 (s, 6H).

HPLC (4.6×150 mm Zorbax SB-C8 column [Agilent], 3.5μ thickness, 95:5 methanol:water (containing 0.1% trifluoroacetic acid) for 10 min, detection at 325 nm): $t_R$ 6.6 min (retinyl O-salicyloylglycolate); $t_R$ 5.3 min (retinyl bromoacetate).

Example 8

Preparation of Retinyl O-Salicyloylglycolate (EX001013-161)

Salicylic acid (33.1 g; 0.24 mol; 1.2 equiv) was combined with 190 mL of nitrogen-purged ethyl acetate in a 1-L reactor at 20° C. Triethylamine (41.8 mL; 0.30 mol; 1.5 equiv) was added to afford a homogeneous solution with an attendant exotherm to 38° C. The mixture was cooled to 20° C., and retinyl bromoacetate (81.4 g; 200 mmol) dissolved in 75 mL of purged ethyl acetate was added over 15 min with a slight exotherm (to 21.4° C.) and then washed in with 15 mL of ethyl acetate. The mixture was stirred for 19 h at room temperature during which a significant amount of precipitate was formed and HPLC analysis indicated >99.5% conversion to product. The mixture was washed with water (280 mL) and then diluted with 280 mL of ethyl acetate. The organic solution was washed with 1:1 methanol:1.5M HCl, then with 5% aqueous sodium bicarbonate (250 mL). The organic phase was dried with magnesium sulfate and concentrated in vacuo to give the desired product as a thick yellow oil (82.47 g; 89% yield).

Example 9

Preparation of Retinyl O-Nicotinoylglycolate

Nicotinic acid (5.171 g; 42.0 mmol) was mixed with N,N-diisopropylethylamine (7.0 mL; 40.2 mmol) in dimethyl formamide (60 mL). The mixture was stirred for 5 min and then placed in a cold bath. At −8° C., retinyl bromoacetate (14.555 g; 35.7 mmol) in dimethyl formamide (15 mL) was added dropwise. The yellow solution was stirred overnight at room temperature. The resulting orange solution was then poured into 150 mL diethyl ether and washed in with 50 mL diethyl ether. After being washed with water (20 mL×3) and 5% sodium bicarbonate (20 mL), the organic phase was dried and concentrated in vacuo to give the desired product as a pale orange yellow solid (13.4 g; 85%). $^1$H NMR (CDCl$_3$) δ (ppm): 9.29 (d, 1H, d=0.9 Hz), 8.84-8.79 (m, 1H), 8.4-8.3 (m, 1H), 7.47-7.39 (m, 1H), 6.67 (dd, 1H, J=15.0, 11.4 Hz), 6.27 (d, 1H, J=15.0 Hz), 6.2-6.0 (m, 3H), 5.61 (t, 1H, J=7.5 Hz), 4.90 (s, 2H), 4.87 (d, 2H, J=7.8 Hz), 2.02 (t, 2H, J=6.0 Hz), 1.96 (s, 3H), 1.90 (s, 3H), 1.71 (s, 3H), 1.65-1.55 (m, 2H), 1.5-1.4 (m, 2H), 1.02 (s, 6H).

HPLC (4.6×150 mm Zorbax SB-C8 column [Agilent], 3.5µ thickness, 95:5 methanol:water (containing 0.1% trifluoroacetic acid) for 10 min, detection at 325 nm): $t_R$ 5.6 min (retinyl O-nicotinoylglycolate); $t_R$ 5.3 min (retinyl bromoacetate).

Example 10

Synthesis of Retinyl O-(2-Cyano-3,3-diphenyl-acryloyl)glycolate

2-Cyano-3,3-diphenyl acrylic acid (1.2 g, 4.8 mmol, 1.3 eq), 45 wt % potassium hydroxide (0.38 mL, 4.4 mmol, 1.2 eq) and 8 mL water were added to a 50 mL, 3-neck flask equipped with a stir bar, nitrogen bubbler and rubber septum. The mixture was stirred under a flow of nitrogen until a homogeneous solution was obtained (about 10 minutes). Tetraheptylammonium bromide (0.18 g, 0.37 mmol, 0.1 eq) was added and the mixture was stirred for 15 minutes. Retinyl bromoacetate (1.5 g, 3.7 mmol, 1.0 eq) was added in 5 mL of toluene. After 15 minutes the mixture became very thick, but continued to stir well. It was left to stir over night at room temperature, at which point HPLC analysis indicated no retinyl bromoacetate. The mixture was transferred to a separatory funnel using toluene and the bottom water layer removed. The organic layer was washed with 15 mL water, then 15 mL of a saturated sodium bicarbonate solution and dried over sodium sulfate. It was concentrated in vacuo to afford 2.52 g of an orange-colored solid. $^1$H NMR (toluene-d$_8$) δ (ppm): 7.25-6.99 (m, 10H), 6.68 (dd, 1H, J=15.0, 11.4 Hz), 6.35-6.12 (m, 4H), 5.52 (t, 1H, J=7.2 Hz), 4.62 (d, 2H, J=7.2 Hz), 4.25 (s, 2H), 2.02 (t, 2H, J=6.0 Hz), 1.92 (s, 3H), 1.82 (s, 3H), 1.70 (s, 3H), 1.68-1.60 (m, 2H), 1.56-1.48 (m, 2H), 1.16 (s, 6H).

HPLC (4.6×150 mm Zorbax SB-C8 column [Agilent], 3.5µ thickness, 95:5 methanol:water (containing 0.1% trifluoroacetic acid) for 10 min, detection at 325 nm): $t_R$ 6.070 min (retinyl bromoacetate); $t_R$ 6.488 min (retinyl O-(2-cyano-3,3-diphenyl-acryloyl)glycolate).

Example 11

Preparation of Oleyl Bromoacetate

Technical grade oleyl alcohol (85 wt %; 10 g; 37.2 mmol) was combined with Novozym 435 (200 mg) in an amber bottle. Methyl bromoacetate (6.84 g; 44.7 mmol; 1.2 equiv.) was added, and the mixture was sealed and stirred at room temperature overnight to afford about 50% conversion to oleyl bromoacetate. The mixture was then purged with a subsurface stream of nitrogen 2.5 days to afford 98.5% conversion of oleyl alcohol to oleyl bromoacetate according to GC analysis. The mixture was filtered, and the solid was washed with toluene. The filtrate was concentrated to give the desired product as a viscous colorless oil (13.19 g, 91%). The product was used in the subsequent reactions without further purification.

$^1$H NMR (CDCl$_3$) δ 5.35 (m, 2H); 4.17 (t, 2H, J=6.70 Hz); 3.83 (s, 2H); 2.1-1.9 (m, 4H); 1.75-1.55 (m, 2H); 1.45-1.2 (m, 22H); 0.95-0.85 (m, 3H).

Example 12

Preparation of Oleyl Glycolyl 4-Methoxycinnamate

4-Methoxycinnamic acid (229 mg; 1.284 mmol; 1.0 equiv) was slurried in 1 mL of toluene. Triethylamine (195 mg; 1.926 mmol; 1.5 equiv) was added and the mixture was stirred at ambient temperature for 1 h to afford a homogeneous solution. Oleyl bromoacetate (500 mg; 1.284 mmol) was added, and the mixture was stirred at ambient temperature for 3 h to indicate 87% conversion of 4-methoxycinnamic acid to product after 3 h according to HPLC analysis. An additional two days of stirring afforded no further conversion. An additional 0.3 equiv of 4-methoxycinnamic acid was added, and the mixture was stirred overnight, then diluted with toluene, 3 M HCl (2 mL), and ethyl acetate. The bottom aqueous layer was removed, and the top layer was washed with 5 mL of 5% sodium bicarbonate solution. The organic layer was dried and concentrated to afford oleyl glycolyl 4-methoxycinnamate (0.51 g; 82%).

$^1$H NMR (CDCl$_3$) δ 7.73 (d, 1H, J=15.9 Hz); 7.50 (d, 2H, J=8.9 Hz); 6.91 (d, 1H, J=8.9 Hz); 6.40 (d, 1H, J=15.9 Hz); 5.34 (m, 2H); 4.73 (s, 2H); 4.18 (t, 2H, J=6.70 Hz); 3.84 (s, 3H); 2.1-1.9 (m, 4H); 1.75-1.55 (m, 2H); 1.45-1.2 (m, 22H); 0.95-0.85 (m, 3H).

HPLC (4.6×150 mm Zorbax SB-C8 column [Agilent], 3.5µ thickness, 90:10 methanol:water (containing 0.1% trifluoroacetic acid) for 20 min, detection at 325 nm): $t_R$ 1.76 min (4-methoxycinnamic acid); $t_R$ 10.5 min (oleyl glycolyl 4-methoxycinnamate).

Example 13

Preparation of Oleyl Glycolyl Retinoate

Retinoic acid (203 mg; 0.674 mmol; 1.05 equiv) was slurried in 2 mL of toluene. Triethylamine (78 mg; 0.77 mmol; 1.2 equiv) was added, and the mixture was stirred at ambient temperature for 30 min to afford a homogeneous solution. Oleyl bromoacetate (250 mg; 0.642 mmol) was added and the mixture was stirred at ambient temperature overnight to indicate 77% conversion of retinoic acid to product by HPLC analysis. An additional two days of stirring afforded no further conversion. The mixture was diluted with heptanes and washed with 3 M HCl (3 mL). The organic layer was washed with a 1:1 mixture of methanol:10% potassium carbonate (2×6 mL), then with 5% sodium bicarbonate solution (3 mL). The organic layer was dried and concentrated to afford oleyl glycolyl retinoate (0.32 g; 82%).

$^1$H NMR (toluene-d$_8$) δ 6.85 (dd, 1H, J=15.0, 11.4 Hz); 6.30 (d, 1H, J=16.3 Hz); 6.20 (d, 1H, J=16.1 Hz); 6.04 (d, 1H, J=15.0 Hz); 6.02 (d, 1H, J=11.5 Hz); 5.92 (s, 1H); 5.45 (m, 2H); 4.46 (s, 2H); 3.94 (t, 2H, J=6.7 Hz); 2.15-2.0 (m, 7H); 1.95 (t, 2H, J=6.3 Hz); 1.78 (s, 3H); 1.74 (s, 3H); 1.65-1.1 (m, 34H); 1.08 (s, 6H); 0.95-0.85 (m, 6H).

HPLC (4.6×150 mm Zorbax SB-C8 column [Agilent], 3.5µ thickness, 90:10 methanol:water (containing 0.1% trifluoroacetic acid) for 7 min, gradient to 95:5 methanol:water (containing 0.1% trifluoroacetic acid) over 1 min, hold for 18 min, gradient to 100% methanol over 1 min, hold for 14 min, detection at 350 nm): $t_R$ 3.8 min (retinoic acid); $t_R$ 23.6 min (oleyl glycolyl retinoate).

Example 14

Enzymatic Hydrolysis of Oleyl Glycolyl Retinoate

Oleyl glycolyl retinoate (50 mg; 0.082 mmol) was dissolved in 1 mL of toluene. pH 7 Phosphate buffer (1 mL) was added followed by Novozym 435 (50 mg). The mixture was stirred for 1 h at ambient temperature to afford 5% hydrolysis according to HPLC analysis. A control reaction without enzyme showed no hydrolysis.

Example 15

Enzymatic Hydrolysis of Retinyl O-Nicotinoylglycolate

Retinyl O-nicotinoylglycolate (50 mg) was dissolved in toluene (1 mL). An aqueous buffer (pH=7.0, 1 mL) was added, followed by Novozym 435 (25 mg). The mixture was stirred at room temperature. At certain reaction times, the stirrer was stopped, and the mixture was allowed to settle. An aliquot of the top organic layer was taken and analyzed with HPLC to determine the extent of hydrolysis, which was calculated according to the following formula:

Hydrolysis(%)=100×LC Area$_{retinol}$/(LC Area$_{retinol}$+ LC Area$_{retinyl\ O\text{-}nicotinoylglycolate}$)

FIG. 1 shows the extent of hydrolysis over reaction time.

That which is claimed is:

1. An ester of O-substituted hydroxy carboxylic acids having Formula 1:

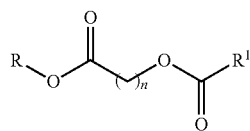

1 wherein
R is retinyl;
$R^1$ is selected from the group consisting of branched- and straight-chain, saturated $C_1$-$C_6$ alkyl; branched- and straight-chain, unsaturated and polyunsaturated $C_2$-$C_{22}$ alkyl; $C_3$-$C_8$ cycloalkyl; $C_6$-$C_{20}$ carbocyclic aryl; and $C_4$-$C_{20}$ heterocyclic group;
the heterocyclic group comprises sulfur, nitrogen, or oxygen;
the heterocyclic group excludes ascorbic acid; and
n is 1-6,
with the proviso that when $R^1$ is a substituted, straight-chain, saturated $C_1$-$C_6$ alkyl, the substituent is selected from the group consisting of $C_1$-$C_6$-alkoxy, carboxyl, amino, $C_1$-$C_{15}$ aminocarbonyl, $C_1$-$C_{15}$ amido, cyano, $C_2$-$C_6$-alkoxycarbonyl, $C_2$-$C_6$-alkanoyloxy, hydroxy, aryl, heteroaryl, thiol, thioether, $C_2$-$C_{10}$ dialkylamino, $C_3$-$C_{15}$ trialkylammonium and halogen.

2. The ester according to claim 1, wherein
$R^1$ is selected from the group consisting of branched- and straight-chain saturated $C_1$-$C_6$ alkyl; branched- and straight-chain $C_2$-$C_{22}$ alkenyl; branched- and straight-chain $C_4$-$C_{22}$ dienyl; branched- and straight-chain $C_6$-$C_{22}$ trienyl; branched- and straight-chain $C_8$-$C_{22}$ tetraenyl; branched- and straight-chain $C_{10}$-$C_{22}$ pentaenyl; $C_3$-$C_8$ cycloalkyl; $C_6$-$C_{20}$ carbocyclic aryl; and $C_4$-$C_{20}$ heterocyclic group.

3. The ester according to claim 2, wherein said alkyl, alkenyl, dienyl, trienyl, tetraenyl, pentaenyl, and cycloalkyl groups are substituted with at least one selected from the group consisting of $C_1$-$C_6$-alkoxy, carboxyl, amino, $C_1$-$C_{15}$ aminocarbonyl, $C_1$-$C_{15}$ amido, cyano, $C_2$-$C_6$-alkoxycarbonyl, $C_2$-$C_6$-alkanoyloxy, hydroxy, aryl, heteroaryl, thiol, thioether, $C_2$-$C_{10}$ dialkylamino, $C_3$-$C_{15}$ trialkylammonium and halogen.

4. The ester according to claim 2, wherein said aryl group is at least one selected from the group consisting of phenyl, naphthyl, and anthracenyl.

5. The ester according to claim 4, wherein said phenyl, naphthyl, or anthracenyl are substituted with at least one substituent selected from the group consisting of $C_1$-$C_6$-alkyl, $C_6$-$C_{10}$ aryl, $C_1$-$C_6$-alkoxy, halogen, carboxy, cyano, $C_1$-$C_6$-alkanoyloxy, $C_1$-$C_6$-alkylthio, $C_1$-$C_6$-alkylsulfonyl, trifluoromethyl, hydroxy, $C_2$-$C_6$-alkoxycarbonyl, $C_2$-$C_6$-alkanoylamino, —O$R^4$, —S—$R^4$, —SO$_2$—$R^4$, —NHSO$_2R^4$, and —NHCO$_2R^4$, wherein $R^4$ is phenyl, naphthyl, or phenyl or naphthyl substituted with one to three groups selected from the group consisting of $C_1$-$C_6$-alkyl, $C_6$-$C_{10}$ aryl, $C_1$-$C_6$-alkoxy, and halogen.

6. The ester according to claim 2, wherein said heterocyclic group is selected from the group consisting of a 5- or 6-membered ring containing one to three heteroatoms selected from the group consisting of oxygen, sulfur, and nitrogen.

7. The ester according to claim 6, wherein said heterocyclic group is at least one selected from the group consisting of pyranyl, oxopyranyl, dihydropyranyl, oxodihydropyranyl, tetrahydropyranyl, thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, pyridyl, pyrimidyl, benzoxazolyl, benzothiazolyl, benzimidazolyl, and indolyl.

8. The ester according to claim 6, wherein said heterocyclic group is substituted with at least one substituent selected from the group consisting of $C_1$-$C_6$-alkyl, $C_1$-$C_6$-alkoxy, halogen, $C_1$-$C_6$-alkylthio, aryl, arylthio, aryloxy, $C_2$-$C_6$-alkoxycarbonyl, and $C_2$-$C_6$-alkanoylamino.

9. The ester according to claim 6, wherein said heterocyclic group is substituted with a fused ring system.

10. The ester according to claim 1, wherein
n is 1, and
$R^1$ is selected from the group consisting of shikimoyl, 4-methoxycinnamoyl, feruloyl, salicyloyl, nicotinoyl, retinoyl, and 2-cyano-3,3-diphenylacryloyl.

11. A cosmetic composition comprising the ester of claim 1.

12. The ester according to claim 1, wherein
n is 1 to 6, and
$R^1$ is selected from the group consisting of shikimoyl, 4-methoxycinnamoyl, feruloyl, salicyloyl, nicotinoyl, retinoyl, and 2-cyano-3,3-diphenylacryloyl.

* * * * *